United States Patent [19]

Gormley

[11] 4,367,360

[45] Jan. 4, 1983

[54] METHOD FOR PRODUCT ISOLATION AND CATALYST RECOVERY IN ALUMINUM CHLORIDE CATALYZED ISOMERIZATION OF SYM-OCTAHYDROPHENANTHRENE TO SYM-OCTAHYDROANTHRACENE

[75] Inventor: William T. Gormley, Pittsburgh, Pa.

[73] Assignee: Koppers Company, Inc., Pittsburgh, Pa.

[21] Appl. No.: 303,543

[22] Filed: Sep. 18, 1981

[51] Int. Cl.$^3$ .............................................. C07C 5/22
[52] U.S. Cl. .................... 585/477; 585/317; 585/318; 585/360
[58] Field of Search ............... 585/471, 477, 480, 481, 585/482, 315, 317, 318, 360; 252/442

[56] References Cited

U.S. PATENT DOCUMENTS

| | | | |
|---|---|---|---|
| 3,295,922 | 1/1967 | Walker | 585/477 |
| 3,396,203 | 8/1968 | Bushick | 585/481 |
| 3,637,882 | 1/1972 | Bushick | 585/477 |

FOREIGN PATENT DOCUMENTS

| | | | |
|---|---|---|---|
| 694961 | 5/1950 | United Kingdom | 585/477 |
| 2065698 | 12/1980 | United Kingdom | 585/477 |

OTHER PUBLICATIONS

Arnold et al., J. Am. Chem. Soc., 66, 960 (1944).

*Primary Examiner*—Delbert E. Gantz
*Assistant Examiner*—A. Pal
*Attorney, Agent, or Firm*—Oscar B. Brumback; J. Timothy Keane

[57] ABSTRACT

A method is disclosed for extracting sym-octahydroanthracene (s-OHA) from a product isomer mixture formed by the aluminum chloride catalyzed isomerization of sym-octahydrophenanthrene (s-OHP). Isolation of the s-OHA product isomer is accomplished by contacting the reaction product mixture with a specified liquid hydrocarbon solvent into which the s-OHA product isomer and unconverted s-OHP isomer dissolve and separate from a residue. The undissolved residue comprises a complex made up of aluminum chloride catalyst and small amounts of the s-OHA and s-OHP isomers. This catalyst complex may be recycled into a fresh starting mixture of s-OHP isomer for catalysis of a subsequent s-OHP isomerization reaction.

14 Claims, No Drawings

METHOD FOR PRODUCT ISOLATION AND CATALYST RECOVERY IN ALUMINUM CHLORIDE CATALYZED ISOMERIZATION OF SYM-OCTAHYDROPHENANTHRENE TO SYM-OCTAHYDROANTHRACENE

BACKGROUND OF THE INVENTION

1. Field of the Invention

Isomerization of sym-octahydrophenanthrene (s-OHP) to sym-octahydroanthracene (s-OHA) in the presence of AlCl$_3$ catalyst is well known. Of particular interest herein are methods for providing increased yields of pure s-OHA and recovery of AlCl$_3$ catalyst in the isomerization of s-OHP to s-OHA.

2. State of the Art

Anthracene is a starting material in a commercially-viable process for making anthraquinone. In addition to use in preparation of dyestuffs, anthraquinone is being used increasingly as a delignification catalyst in paper pulping processes. Anthracene is found naturally in coal tar at a concentration of about 1 to 3 weight percent of all coal-tar hydrocarbons. About one-half of this amount of anthracene is recoverable by commercial distillation and crystallization methods. Phenanthrene, an isomer of anthracene, is found in coal tar at a concentration of about five weight percent of all coal-tar hydrocarbons. Since phenanthrene is more abundant that anthracene, much attention has been given to conversion of phenanthrene to anthracene.

The only known conversion of phenanthrene to anthracene involves three steps. Firstly, phenanthrene is catalytically hydrogenated to sym-octahydrophenanthrene (s-OHP); secondly, s-OHP undergoes catalyzed isomerization to sym-octahydroanthracene (s-OHA); and thirdly, s-OHA is dehydrogenated to anthracene. In the second-step of isomerization of s-OHP to s-OHA, in the presence of AlCl$_3$ as the isomerization catalyst, all known isomerization reactions provide relatively low yields of the desired s-OHA isomer or relatively high by-product impurities.

For example, a 1924 German publication (G. Schroeter, Ber. 57B, 1990–2003) discloses a reversible isomerization reaction starting with either pure s-OHP or pure s-OHA isomer. In this reversible reaction, 50 percent yields of both s-OHP and s-OHA are obtained from either starting isomer in the presence of small amounts of AlCl$_3$ at an isomerization temperature in a range of 70° to 80° C.

In U.K. Pat. No. 694,961 s-OHP is isomerized to s-OHA in the presence of dispersed, finely-divided AlCl$_3$ catalyst at an isomerization temperature in a range of 5° to 45° C. Dilution of the reaction products with toluene and subsequent hydrolysis with aqueous hydrochloric acid provides a toluene layer containing the s-OHP and s-OHA isomers. Acid hydrolysis precludes reuse of the AlCl$_3$ catalyst and s-OHA yield ranged from about 70 to 83 weight percent in the presence of about 10 to 13 weight percent unidentified by-products.

A 1978 West German publication [K. Handrick et al., "Production of Anthracene from Phenanthrene," Compend.-Dtsch. Ges. Kohlechem., 78–79(2), 1089–1106] describes a starting mixture containing s-OHP in the presence of about six weight percent s-OHA; after isomerization, the reaction product mixture contains an equilibrium mixture of s-OHP and s-OHA isomers, there being about 50 to 60 weight percent s-OHA present.

Prior art isomerization processes provide relatively low yields of the desired sym-octahydroanthracene isomer or provide relatively large amounts of unwanted by-products. Moreover, where an aqueous-acid hydrolysis step is used to isolate the desired isomer, AlCl$_3$ catalyst is decomposed and thus rendered ineffective for further catalysis. There is need, therefore, for s-OHP to s-OHA isomerization processes characterized by improved methods for separation and recovery of s-OHA product or AlCl$_3$ catalyst.

SUMMARY OF THE INVENTION

In an isomerization process as outlined in Equation I for converting sym-octahydrophenanthrene (s-OHP) to sym-octahydroanthracene (s-OHA) in the presence of a catalyst comprising AlCl$_3$, or AlBr$_3$, or a mixture of AlCl$_3$ and AlBr$_3$, there are provided improvements in the isolating of the s-OHA product isomer from a reaction products mixture.

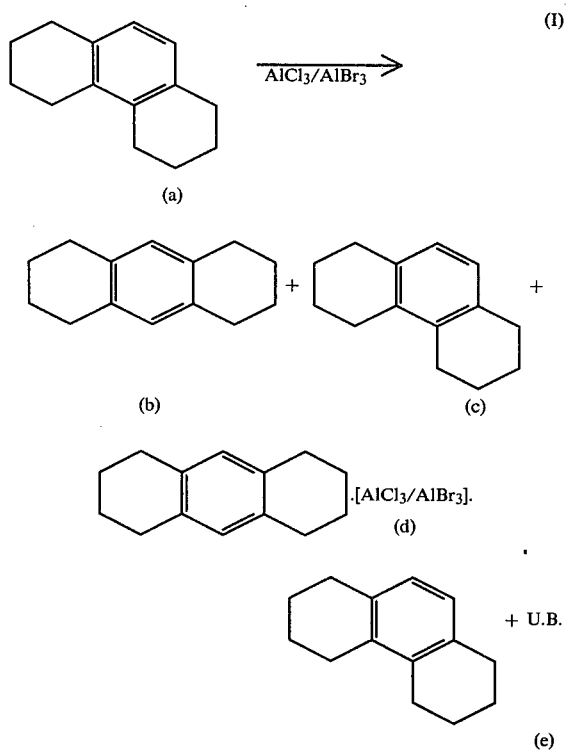

Isomerization of s-OHP starting isomer (a) in the presence of AlCl$_3$/AlBr$_3$ catalyst provides a reaction product mixture containing a major amount of free s-OHA product isomer (b), a minor amount of free unconverted s-OHP starting isomer (c), a three-component isomer-catalyst complex (d) consisting essentially of unconverted s-OHP, s-OHA product and the AlCl$_3$ or AlBr$_3$ catalyst, and a small amount of unidentified by-products of an organic nature (e). Extraction of s-OHA product isomer is accomplished by contacting the reaction product mixture with a solvent provided by a saturated aliphatic or cycloaliphatic liquid hydrocarbon having a boiling point in a range from about 30° C. to about 160° C. Free, unconverted s-OHP starting isomer and free s-OHA product isomer dissolve into the liquid hydrocarbon solvent and are thereby separated, or isolated, from other components of the reaction-product mixture. Subsequent removal of the solvent from the isolated s-OHA and s-OHP isomers provides, after an optional fractional crystallization step, s-OHA isomer virtually free of impurities; the minor amount of unconverted s-OHP dissolved in the liquid hydrocarbon solvent is pure enough for recycling directly into a starting mixture for another isomerization step.

After separation of free s-OHP and free s-OHA isomers from the reaction product mixture by dissolving of the isomers into the liquid hydrocarbon solvent, there remains a semi-solid residue containing the isomer-catalyst complex and a small amount of unidentified by-products. The process of the invention is further characterized by a step of forming a second starting mixture comprising fresh s-OHP and the semi-solid residue containing the isomer-catalyst complex. This second starting mixture is subjected to the isomerization reaction in the presence of "used" or "recycled" catalyst from the semi-solid residue to provide a second reaction product mixture containing s-OHA product isomer and unconverted s-OHP starting isomer. Extraction of these isomers is accomplished by the above-described contacting step utilizing the liquid hydrocarbon solvent.

Compared to previously reported isomerization processes, the instant process provides relatively higher conversion of s-OHP starting isomer into s-OHA product isomer and also relatively higher yields of a purer reaction product mixture containing both s-OHA and s-OHP isomers with relatively less unwanted by-product. The isolated s-OHA and s-OHP isomer mixture is pure enough to be subjected directly to dehydrogenation to form anthracene, with the small amount of phenanthrene formed being easily separable by known techniques. Another significant advantage of the invention is the reduction of undesirable or useless by-products contained in the reaction product mixture; such undesirable by-products may impart dark color to the product mixture or may inactivate the isomerization catalyst. Still another important advantage is that extraction of the free s-OHA and s-OHP isomers is accomplished without destruction or inactivation of the $AlCl_3$ catalyst. Thus, used $AlCl_3$ or $AlBr_3$ catalyst may be recycled into a second or subsequent batches of the starting mixture. Recycling of unconverted s-OHP starting isomer and used $AlCl_3$ or $AlBr_3$ catalyst makes possible a semi-continuous process for making s-OHA isomer.

DETAILED DESCRIPTION OF THE INVENTION

In providing a starting mixture comprising s-OHP starting isomer and $AlCl_3$ or $AlBr_3$ catalyst, or a mixture of the two catalysts, the starting isomer and catalyst are charged to a reaction vessel equipped with stirring means. An amount of catalyst may be used from about 4 to about 50 weight percent based upon the total weight of the s-OHP isomer in the starting mixture. More typically, about 5 to about 15 weight percent catalyst is used. Practically any commercially-prepared grade of sym-octahydrophenanthrene may be used as a starting material for conversion to sym-octahydroanthracene in the process of the invention. Typically useful s-OHP starting isomer is prepared by hydrogenation of desulfurized phenanthrene over nickel catalyst by procedures such as shown in U.S. Pat. No. 3,389,188. Commercial grades of aluminum chloride and aluminum bromide are suitable for use as an isomerization catalyst, such as sold by Aldrich Chemical Co., Milwaukee, Wis., and Fisher Scientific Co., Pittsburgh, Pa. Finer particle size materials are preferred over coarser materials. Practically any conventional mechanical mixer, such as a ball mill or a double-arm mixer, may be used as a reactor for the isomerization reaction; examples of useful double-arm mixers include a double-arm sigma blade mixer and an Atlantic helical-action mixer, with the latter type generally preferred. The s-OHP starting isomer is a liquid at room temperature and the $AlCl_3$ or $AlBr_3$ catalyst is in the form of a finely-divided powder. The highest conversions of starting isomer are obtained by ensuring even distribution of the catalyst powder throughout the starting isomer to aid in complexation of the catalyst with the s-OHP isomer. Even distribution is accomplished by thorough mixing of the s-OHP isomer and the catalyst in the mechanical mixer.

In allowing the starting mixture to react, isomerization of s-OHP isomer to s-OHA isomer typically takes place in two stages, namely, a mixing stage and a standing stage. During the mixing and standing stages, the s-OHP starting isomer and catalyst are maintained in intimate contact for a period of time and at a temperature sufficient to convert at least about 70 weight percent of the s-OHP starting isomer to s-OHA product isomer. After charging of the liquid s-OHP isomer and catalyst powder to the mechanical mixer, the isomer and catalyst are mixed together for about two hours. Generally, mixing occurs with no heat being added except for the waste heat contributed by the mechanical mixer and by the movement of the isomer and catalyst within the reactor. The temperature of the reaction mass is thus typically maintained at about 25° C. during the mixing and standing stages, although reaction temperatures as high as 40° C. and as low as 20° C. may be used with practicality.

After approximately two hours of mixing, a semi-solid mass is formed. This semi-solid reaction mass, typically reddish-brown or dark brown in color, contains free, unconverted s-OHP starting isomer and free s-OHA product isomer. The reaction mass is usually thickened sufficiently after about two hours of mixing so that the dispersed catalyst remains suspended in the reaction mass. Upon achievement of a thickened state of the reaction mass, mixing is usually discontinued inasmuch as conventional mechanical mixers have insufficient mixing capacity to continue movement of the reaction mass. Thereafter, a second stage, the standing stage, of the isomerization process begins.

In the standing stage, the reaction mass is allowed to stand for several hours after the thickened state is achieved. Occasional mixing of the reaction mass may occur during the standing stage, although mixing is not generally required for reaction to proceed. Typically, the reaction mass is maintained in the thickened state for a period of time from about two hours to about four hours, although periods as long as 48 hours may be utilized. During the standing stage, isomerization of s-OHP isomer to s-OHA isomer continues to produce a significant amount of s-OHA product isomer.

At the end of the reaction period, the semi-solid mass provides a reaction-product mixture containing a major amount of free s-OHA product isomer, a minor amount of free, unconverted s-OHP isomer, and a three-component complex consisting of unconverted s-OHP, s-OHA product isomer and the used catalyst. Separation of the free s-OHA and s-OHP isomers from the semi-solid mass is accomplished by contacting the semi-solid mass with a suitable liquid hydrocarbon solvent. The contacting step is accomplished by adding and mixing the liquid hydrocarbon solvent into the semi-solid mass, usually at about 25° C. Typically, the liquid hydrocarbon is added in an amount in a volume-ratio-range from about one-to-one to about four-to-one of liquid hydrocarbon solvent to the semi-solid mass. After addition and mixing of the liquid hydrocarbon solvent into the semi-solid mass, a liquid phase is formed in contact with undissolved material. The free s-OHP and s-OHA isomers are dissolved into the liquid phase and thereby separated from the solid residue material; this residue material contains the isomer-catalyst complex and a small amount of unidentified by-product.

A liquid hydrocarbon solvent useful for adding to the semi-solid reaction mass to form a liquid phase in contact with undissolved residue material may be selected from easily-recoverable, non-reactive aliphatic or cycloaliphatic hydrocarbons. The phrase "easily-recoverable, non-reactive" is intended to characterize hydrocarbons which may be easily removed from the dissolved isomers, such as by evaporation, and which hydrocarbons do not form complexes with the catalyst, or with the dissolved isomers, or with other constituents of the reaction-product mixture, and further do not dissolve the catalyst. Liquid hydrocarbons satisfying these criteria are typically those which are liquid at about 25° C. and have a boiling point in a range from about 30° C. to about 160° C.; preferably, useful hydrocarbons will have a boiling point from about 30° C. to about 100° C. Examples of suitable aliphatic hydrocarbons are n-pentane, n-hexane, n-decane, n-undecane, 2,2,4-trimethylpentane and petroleum ether mixtures. Examples of suitable cycloaliphatic hydrocarbons are cyclohexane, methylcyclohexane and 1,4-dimethylcyclohexane. A preferred liquid hydrocarbon is n-hexane.

The hydrocarbon-solvent liquid phase containing free unconverted s-OHP starting isomer and free s-OHA product isomer is separated from the undissolved residue material by decanting or by centrifugal separation. A resulting residue may then be washed with subsequent portions of the hydrocarbon solvent, which portions are separated from the undissolved residue and combined with the original hydrocarbon-solvent liquid phase. The s-OHP and s-OHA isomers are isolated from the liquid phase by evaporation of the hydrocarbon solvent under reduced pressure, or under a gas stream, with or without the addition of heat. If heat is used to aid in evaporation of the liquid solvent, the temperature of the evaporating liquid should not exceed about 150° C. After removal of the liquid hydrocarbon, there typically remains an off-white liquid which upon cooling to room temperature converts to opaque-white flaky crystals. Separation of the s-OHA and s-OHP isomers from each other is accomplished, if necessary, by fractional crystallization utilizing known techniques.

As another embodiment of the invention, a second or subsequent starting mixture may be provided comprising a fresh bath of s-OHP starting isomer along with an amount of semi-solid residue formed from the first or preceding starting mixture. This semi-solid residue, which contains used catalyst from the first or preceding isomerization reaction, may be reused as the isomerization catalyst for the second or subsequent isomerization reaction. Reuse or cycling of the catalyst into a series of isomerization reactions allows for a semi-continuous process for making s-OHA from s-OHP.

In still another embodiment of the invention, a second or subsequent starting mixture is provided by a fresh batch of s-OHP starting isomer, which mixture is enriched with s-OHA product isomer in an amount in a range from about 10 to about 50 weight percent of the starting mixture. Enrichment of a starting mixture with s-OHA may be accomplished by utilizing portions of the reaction product mixture formed in the first or preceding isomerization reaction. For example, a recycle portion may be provided by a residue containing s-OHP and s-OHA which remains after fractional crystallization of the isomers. Or, a recycle portion may be provided by a residue containing s-OHA and s-OHP isomers mixed with the catalyst-isomer complex which remains from incomplete separation of free unconverted s-OHP isomer and s-OHA product isomer in a preceding isomerization reaction. Cycling of a portion of the reaction product mixture back into a starting mixture allows for a semi-continuous process for making s-OHA from s-OHP with little or no waste of starting or product isomers.

The residue, containing s-OHA and s-OHP isomers, a catalyst-isomer complex and unidentifed organic by-products, may be further treated to recover additional amounts of s-OHA product isomer and unconverted s-OHP starting isomer. This residue, typically brown in color, may be dissolved in a two-phase solvent system, such as provided by water and a water-immiscible organic solvent. A suitable solvent may be practically any water-immiscible aliphatic or aromatic solvent. For example, hexane and water may be used as a suitable two-phase solvent system. When the residue and the water-hexane two-phase solvent system are brought together, the catalyst-isomer complex decomposes. The organic components, including the s-OHA and s-OHP isomers and unidentified by-products, dissolve into the hexane phase and the $AlCl_3$ component dissolves into the water phase. Separation of the water and hexane phases and subsequent removal of the hexane solvent provides amounts of s-OHP and s-OHA isomers which may be separated and purified from the organic by-products by conventional, fractional crystallization techniques.

Surprisingly, in the presence of an enriched starting mixture containing equal portions of s-OHP and s-OHA isomers, low-temperature isomerization of s-OHP to s-OHA proceeds substantially to completion without loss of s-OHA by reverse isomerization to s-OHP. Heretofore, it has been reported that reverse isomerization occurs in starting mixtures containing large amounts of s-OHA. Substantially complete isomerization of an s-OHP mixture enriched with s-OHA is of significant advantage inasmuch as some sources of hydrogenated phenathrene may contain relatively large amounts of s-OHA isomer.

The following examples set forth specific embodiments of the invention. The invention is not to be construed, however, as being limited to these embodiments for there are, of course, numerous possible variations and modifications. All parts and percentages of the examples as well as throughout the specification are by weight unless otherwise indicated.

EXAMPLE I

To a glass reaction vessel equipped with magnetic-type stirring means, there was charged 1.35 g reagent grade anhydrous AlCl₃ together with 13.5 g of water-white liquid sym-octahydrophenathrene (s-OHP); this s-OHP isomer was prepared by hydrogenation of desulfurized phenanthrene over nickel catalyst. These components were maintained in a magnetically-stirred, closed reaction vessel for about 48 hours at room temperature. Initially, the reaction vessel had a head space of about one-half the total volume of the reaction vessel. No exothermic condition was noted, but the viscosity of the reaction mass increased to an extent sufficient to stop the magnetic stirrer after about two hours. At the end of the 48-hour reaction period, the last 46 hours of which may be considered the "standing" stage of the isomerization reaction, a reddish-brown semi-solid mass was observed having a volume approximately equal to the original starting materials. Then about 25 ml of hexane was added to the semi-solid mass with mechanical stirring of the mass. The addition of hexane provided a clear solution in contact with a small amount of brown residue at the bottom of the reaction vessel. The clear solution was decanted into a collection vessel. Then, three more additions of 25 ml hexane each were added serially to the residue in the reaction vessel with stirring, and then the resulting solutions were decanted into the collection vessel to give a total hexane solution of approximately 100 ml. The hexane-washed brown residue was retained for further disposition. The contents of the collection vessel were transferred to a Rinco rotary evaporator, and hexane was evaporated completely from the contents of the rotary evaporator at 80 mm pressure absolute and with the temperature increasing by heating from room temperature to about 80° C. over a one-hour evaporation period. At the end of the evaporation period, a concentrated extract was observed in the reaction vessel as an off-white liquid at about 80° C. Upon cooling of the off-white liquid to room temperature, opaque-white, flaky crystals formed in an amount of 10.1 g.

NMR analysis of the crystals formed from the concentrated extract showed a product containing 87 percent by weight of sym-octahydroanthracene and 11 percent sym-octahydrophenanthrene with 2 percent unidentified residual material.

EXAMPLE II

To a glass reaction vessel equipped with magnetic-type stirring means and containing the hexane-washed brown residue of Example I, there was charged 13.5 g of water-white liquid sym-octahydrophenathrene (s-OHP); this s-OHP was prepared by hydrogenation of desulfurized phenanthrene over nickel catalyst. These components were maintained in a magnetically-stirred, closed reaction vessel for about 48 hours at room temperature. Initially, the reaction vessel had a head space of about one-half the total volume of the reaction vessel. No exothermic condition was noted, but the viscosity of the reaction mass increased to an extent sufficient to stop the magnetic stirrer after about two hours. At the end of the 48-hour reaction period, a reddish-brown semi-solid mass was observed having a volume approximately equal to the original starting materials. Then about 20 ml of hexane was added to the semi-solid mass with mechanical stirring. The addition of hexane provided a clear solution in contact with a small amount of brown residue at the bottom of the reaction vessel. The clear solution was decanted into a collection vessel. Then, two more additions of 20 ml hexane each were added serially to the residue in the reaction vessel with stirring and then the resulting solutions were decanted into the collection vessel to give a total hexane solution of approximately 60 ml containing the reaction product. The hexane-washed brown residue was discarded. The contents of the collection vessel were transferred to a Rinco rotary evaporator, and hexane was evaporated completely from the contents of the rotary evaporator at 80 mm pressure absolute and with the temperature increasing by heating from room temperature to about 80° C. over a one-hour evaporation period. At the end of the evaporation period, a concentrated extract was observed in the reaction vessel as an off-white liquid at about 80° C. Upon cooling of the off-white liquid to room temperature, opaque-white, flaky crystals formed in an amount of 13.2 g.

NMR analysis of the crystals formed from the concentrated extract showed a product containing 84 percent by weight of sym-octahydroanthracene and 13 percent sym-octahydrophenanthrene with 3 percent unidentified residual material.

EXAMPLE III

To a reaction vessel there was charged 2.16 g reagent grade anhyrous AlCl₃ together with 21.6 g of sym-octahydrophenanthrene (s-OHP) in crystalline form at 10° C.; the s-OHP charge was prepared by hydrogenation of desulfurized phenanthrene over nickel catalyst. These components were stirred mechanically with the reaction vessel open to the atmosphere for about two minutes at room temperature to form a semi-solid reddish paste having the AlCl₃ dispersed evenly throughout the paste. The reddish paste was stored for about four hours at 10° C. with the reaction vessel closed to the atmosphere. Then about 25 ml of hexane was added to the paste with stirring. The addition of hexane provided a clear solution in contact with a small amount of brown residue at the bottom of the reaction vessel. The clear solution was decanted into a collection vessel. The hexane addition-decanting steps were repeated twice using 25 ml volumes of hexane to provide in the collection vessel approximately 75 ml of hexane containing the reaction products. The hexane-washed brown residue was retained for further disposition. Hexane was evaporated substantially completely from the collection vessel under a nitrogen stream. At the end of the evaporation period, a concentrated extract weighing 20.1 g was observed in the collection vessel consisting of a solid material in contact with a liquid.

NMR analysis of the concentrated extract showed a product containing 15 weight percent syn-octahydroanthracene and 82 weight percent sym-octahydrophenanthrene in the presence of 3 weight percent unidentified residual material. The relatively low conversion of s-OHP to s-OHA was attributed to the relatively low reaction temperature.

In order to demonstrate the catalyst recycle/re-use aspects of the invention, additional s-OHP to s-OHA isomerization reactions were conducted in the presence of the previously-isolated hexane-washed brown residue which contained AlCl₃ catalyst. The second series of isomerization reaction-and-product isolation steps were conducted generally as described for the first series, except that 15.4 g of newly-added s-OHP starting material was used and the reaction was allowed to proceed for 18 hours at 25° C. In a third series of isomerization-and-product isolation steps, 9.2 g of newly-added s-OHP starting material was allowed to react for 6 hours at 25° C., there having been added 1.1 g of fresh make-up AlCl₃ catalyst to the previously-used AlCl₃. A fourth and fifth series of isomerization-isolation steps were performed utilizing recycled AlCl₃ catalyst. Summarized in Table I below are data describing reaction parameters and products for the five series of isomerization-isolation steps.

TABLE I

| sym-OHP | AlCl₃ | Reaction | | Product Recovery | | Product Analysis, mole percent | | |
|---|---|---|---|---|---|---|---|---|
| g. | g. | Hrs. | T.°C. | g. | % | s-OHA | s-OHP | Other |
| 21.6 | 2.16 | 4 | 10 | 20.1 | 98 | 15 | 82 | 3 |
| 15.4 | — | 18 | 25 | 13.7 | 89 | 87 | 11 | — |
| 9.2 | Add 1.1 | 6 | 25 | 7.5 | 82 | 80 | 16 | 4 |
| 7.6 | — | 72 | 25 | 6.0 | 79 | 84 | 13 | 3 |
| 8.2 | — | 24 | 25 | 7.0 | 85 | 50 | 47 | 3 |

EXAMPLE IV

An NMR analysis was made on a brown residue such as remained from the product extraction step of Example I. Prior to NMR analysis of the residue, which is essentially an AlCl₃-organic complex, the residue was dissolved in a water-hexane two-phase system (one-to-one volume ratio). The solvent system decomposed the complex, with AlCl₃ dissolved in water and the organic component dissolved in hexane. The hexane and water solvents were separated. The hexane phase was dried over a desiccant and then hexane was removed from the organic phase by heating the organic phase under a nitrogen stream so as to provide a brown, oily liquid at 80° C. Upon cooling of the oily liquid to room temperature, a dark brown viscous liquid formed in an amount of 3.0 g. NMR analysis of this viscous liquid showed the presence of 34% by weight sym-octahydroanthracene and 36% by weight sym-octahydrophenanthrene with 30% unidentified material.

EXAMPLE V

To a glass reaction vessel equipped with magnetic-type stirring means, there was charged 0.3 g reagent grade anhydrous AlCl₃ together with a slurry made by mixing 6 g of sym-octahydrophenanthrene (s-OHP) with 6 g sym-octahydroanthracene (s-OHA); this s-OHP was prepared by hydrogenation of desulfurized phenanthrene over nickel catalyst, and the s-OHA component was made by hydrogenation of anthracene.

This 50:50 s-OHP:s-OHA starting mixture is comparable to an s-OHA enriched mixture obtained from isomerization of s-OHP by a known, conventional isomerization method. These components were maintained in a magnetically-stirred, closed reaction vessel for about 5 hours at room temperature. Initially, the reaction vessel had a head space of about one-half the total volume of the reaction vessel. No exothermic condition was noted, but the viscosity of the reaction mass increased to an extent sufficient to stop the magnetic stirrer after about three hours. At the end of the 5 hour period, a reddish-brown semi-solid mass was observed having a volume approximately equal to the original starting materials. Then about 20 ml of hexane was added to the semi-solid mass with mechanical stirring. The addition of hexane provided a clear solution in contact with a small amount of brown residue at the bottom of the reaction vessel. The clear solution was decanted into a collection vessel. Then, two more additions of 20 ml hexane each were added serially to the residue in the reaction vessel with stirring, and then the resulting solutions were decanted into the collection vessel to give a total hexane solution of approximately 60 ml containing the reaction product. Hexane was evaporated completely from the collection vessel under a stream of nitrogen without addition of heat. At the end of the evaporation period, the concentrated extract was observed in the collection vessel as a crystalline solid in an amount of 10.8 g.

NMR analysis of the crystals formed from the concentrated extract showed a product containing 78 weight percent sym-octahydroanthracene and 21 weight percent sym-octahydrophenanthrene with 1 percent unidentified residual material.

Although specific examples of the instant invention have been set forth hereinabove, it is not intended that the invention be limited solely thereto, but is to include all the variations and modifications falling within the scope of the appended claims.

What is claimed is:

1. A process for converting sym-octahydrophenanthrene to sym-octahydroanthracene in the presence of catalyst comprising AlCl₃, or AlBr₃, or a mixture thereof, in which process there is formed a reaction-product mixture containing a major amount of free sym-octahydroanthracene, a minor amount of free sym-octahydrophenanthrene, and a three-component complex consisting of unconverted sym-octahydrophenanthrene, sym-octahydroanthracene product and said catalyst, the process comprising:

contacting said reaction-product mixture with a saturated aliphatic or cycloaliphatic liquid hydrocarbon having a boiling point in a range from about 30° C. to about 160° C., whereby the free unconverted sym-octahydrophenanthrene isomer and the free sym-octahydroanthracene product isomer are dissolved in said hydrocarbon.

2. The process of claim 1 wherein said liquid hydrocarbon is contacted with said complex in amounts by volume ratio in a range from about one-to-one to about four-to-one.

3. The process of claim 1 wherein said hydrocarbon is n-hexane.

4. A process for isomerization of sym-octahydrophenanthrene to sym-octahydroanthracene, comprising the steps:

(a) providing a starting mixture comprising sym-octahydrophenanthrene and a catalyst provided by AlCl₃, or AlBr₃, or a mixture thereof;

(b) allowing said starting mixture to react for a period of time and at a temperature sufficient to convert at least about 70 weight percent of the sym-octahydrophenanthrene to sym-octahydroanthracene in the form of a semi-solid mass containing sym-octahydrophenanthrene, sym-octahydroanthracene and said catalyst;

(c) contacting said semi-solid mass with a saturated aliphatic or cycloaliphatic liquid hydrocarbon having a boiling point in a range from about 30° C. to about 160° C. to provide a hydrocarbon liquid phase containing sym-octahydrophenanthrene and sym-octahydroanthracene in contact with a semi-solid residue containing used catalyst, whereby the liquid hydrocarbon phase may be separated from the semi-solid residue, and thereafter relatively pure sym-octahydroanthracene may be obtained by removal of the hydrocarbon and unconverted sym-octahydrophenanthrene.

5. The process of claim 4 wherein said starting mixture is enriched with sym-octahydroanthracene in an amount in a range from about 10 to about 50 weight percent of said starting mixture.

6. The process of claim 4 wherein said liquid hydrocarbon is contacted with said semi-solid mass in relative amounts by volume ratio in a range from about one-to-one to about four-to-one.

7. The process of claim 4 wherein said hydrocarbon is hexane.

8. The process of claim 4 further characterized by:
providing a second starting mixture comprising fresh sym-octahydrophenanthrene and said semi-solid residue containing used catalyst,
whereby relatively pure sym-octahydroanthracene may be formed and isolated in accordance with said steps (b) and (c).

9. The process of claim 4 further characterized by allowing said starting mixture to react at a temperature in a range from about 20° C. to about 40° C.

10. The process of claim 4 further characterized by treating the semi-solid residue with a two-phase solvent system comprising water and a water-immiscible organic solvent, said semi-solid residue comprising residual sym-octahydrophenanthrene and sym-octahydroanthracene isomers, a complex of said isomers and of said used catalyst, and unidentified organic by-products, so that used catalyst dissolves into the water phase and the residual sym-octahydroanthracene and sym-octahydrophenanthrene isomers and unidentified organic by-products dissolve into the organic solvent.

11. A process for converting sym-octahydrophenanthrene to sym-octahydroanthracene comprising
(a) contacting sym-octahydrophenanthrene with a semi-solid consisting of unconverted sym-octahydrophenanthrene, sym-octahydroanthracene and a catalyst that is $AlCl_3$, or $AlBr_3$, or a mixture thereof, to convert a major amount of the sym-octahydrophenanthrene to sym-octahydroanthracene, thereafter (b) dissolving the free unconverted sym-octahydrophenanthrene isomer and the free converted sym-octahydroanthracene isomer in a liquid that is a saturated aliphatic or cycloaliphatic hydrocarbon having a boiling point in a range from about 30° C. to 160° C., and (c) separating the liquid from the semi-solid and repeating the process.

12. The process of claim 11 wherein the ratio of the volume of liquid hydrocarbon to be used to the volume of semi-solid is from about one-to-one to about four-to-one.

13. The process of claim 12 wherein said liquid hydrocarbon is n-hexane.

14. A process for isomerization of sym-octahydrophenanthrene to sym-octahydroanthracene, comprising the steps:
(a) contacting a sym-octahydrophenanthrene isomer with a catalyst provided by $AlCl_3$, or $AlBr_3$, or a mixture thereof, for a period of time and at a temperature sufficient to isomerize a major amount of the sym-octahydrophenanthrene isomer to the sym-octahydroanthracene isomer and form a semi-solid mass containing both the sym-octahydrophenanthrene and sym-octahydroanthracene isomer and the catalyst; then (b) contacting said semi-solid mass with a saturated aliphatic or cycloaliphatic liquid hydrocarbon having a boiling point in a range from about 30° C. to 160° C. to provide a hydrocarbon liquid phase containing sym-octahydrophenanthrene and sym-octahydroanthracene isomers and a semi-solid phase containing used catalyst, (c) Separating the liquid hydrocarbon phase from the semi-solid phase; and thereafter (d) contacting additional sym-octahydrophenanthrene with said semi-solid phase to isomerize a major amount of the additional sym-octahydrophenanthrene isomer to the sym-octahydroanthracene isomer, whereby steps (b), (c) and (d) may be repeated.

* * * * *